(12) United States Patent
Fukushima et al.

(10) Patent No.: US 11,273,212 B2
(45) Date of Patent: Mar. 15, 2022

(54) MALARIA VACCINE

(71) Applicants: Sumitomo Dainippon Pharma Co., Ltd., Osaka (JP); NATIONAL UNIVERSITY CORPORATION EHIME UNIVERSITY, Ehime (JP)

(72) Inventors: Akihisa Fukushima, Osaka (JP); Takafumi Tsuboi, Matsuyama (JP); Eizo Takashima, Matsuyama (JP); Hikaru Nagaoka, Matsuyama (JP)

(73) Assignees: Sumitomo Dainippon Pharma Co., Ltd., Osaka (JP); National University Corporation Ehime University, Ehime (JP)

( * ) Notice: Subject to any disclaimer, the term of this patent is extended or adjusted under 35 U.S.C. 154(b) by 0 days.

(21) Appl. No.: 16/348,803

(22) PCT Filed: Nov. 10, 2017

(86) PCT No.: PCT/JP2017/040532
§ 371 (c)(1),
(2) Date: May 9, 2019

(87) PCT Pub. No.: WO2018/088507
PCT Pub. Date: May 17, 2018

(65) Prior Publication Data
US 2019/0343943 A1 Nov. 14, 2019

(30) Foreign Application Priority Data

Nov. 11, 2016 (JP) .............................. JP2016-220512
Aug. 24, 2017 (JP) .............................. JP2017-161442

(51) Int. Cl.
| A61K 39/015 | (2006.01) |
| A61P 33/06  | (2006.01) |
| A61K 39/05  | (2006.01) |
| A61K 39/13  | (2006.01) |
| C07K 14/445 | (2006.01) |
| C07K 16/20  | (2006.01) |
| C12N 15/10  | (2006.01) |

(52) U.S. Cl.
CPC ............ *A61K 39/015* (2013.01); *A61K 39/05* (2013.01); *A61K 39/13* (2013.01); *A61P 33/06* (2018.01); *C07K 14/445* (2013.01); *C07K 16/205* (2013.01); *C12N 15/1006* (2013.01)

(58) Field of Classification Search
None
See application file for complete search history.

(56) References Cited

U.S. PATENT DOCUMENTS 9,109,040 B2  8/2015 Chen et al.
9,884,101 B2  2/2018 Chen et al.
2014/0010816 A1  1/2014 Chen et al.
2014/0093540 A1  4/2014 Wright et al.
2015/0366958 A1 12/2015 Chen et al.
2017/0106071 A1  4/2017 Boes et al.

FOREIGN PATENT DOCUMENTS

| CN | 103260641      | 8/2013  |
| EP | 2624861 A1     | 8/2013  |
| EP | 2923709 A1     | 9/2015  |
| JP | H09122476      | 5/1997  |
| JP | 2017512498     | 5/2017  |
| KR | 20130129215    | 11/2013 |
| WO | WO 2003064671  | 8/2003  |
| WO | WO 2005030954  | 4/2005  |
| WO | WO 2012046081  | 4/2012  |
| WO | WO 2012061882  | 5/2012  |
| WO | WO 2014174054  | 10/2014 |
| WO | WO 2015144874  | 10/2015 |

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Arumugam et al., "Discovery of GAMA, a Plasmodium falciparum Merozoite Micronemal Protein, as a Novel Blood-Stage Vaccine Candidate Antigen," Infection and Immunity, Sep. 2011, 79(11):4523-4532.
ASTMH.com [Online], "ASTMH 2017 Annual Meeting," Nov. 5-9, 2017, retrieved Jul. 18, 2019, retrieved from URL <https://www.astmh.org/ASTMH/media/2017-annual-meeting/ASTMH-17-Reg-Brochusre-FNL.pdf#search=%27ASTMH+66th+annual+meeting%2C+Baltimore%2C+USA%2C+November+59%2C+2017%27.
Azuma, "Biologically Active Components from Mycobacterial Cell Walls. I. Isolation and Composition of Cell Wall Skeleton and Component P3," JNCI: Journal of the National Cancer Institute, 1974, 52(1):95-101.
Barclay et al. "Effects of Oil-treated Mycobacterial Cell Walls on the Organs of Mice," J Bacteriol, 1967, 1736-1745.
Bowman et al., "The Complete Nucleotide Sequence of Chromosome 3 of Plasmodium falciparum," Nature, Aug. 1999, 400(6744):532-538.

(Continued)

*Primary Examiner* — Robert A Zeman
(74) *Attorney, Agent, or Firm* — Fish & Richardson P.C.

(57) ABSTRACT

The present invention relates to a polypeptide consisting of an amino acid sequence selected from:
(a) the amino acid sequence of SEQ ID NO: 4 or SEQ ID NO: 8,
(b) an amino acid sequence that differs from the amino acid sequence of SEQ ID NO: 4 or SEQ ID NO: 8 by substitution, deletion, addition, or insertion of 1 to 10, preferably 1-5, more preferably 1, 2 or 3 amino acids, and
(c) an amino acid sequence that has at least 95%, preferably 97%, more preferably 99% sequence identity with the amino acid sequence of SEQ ID NO: 4 or SEQ ID NO: 8, and a malaria vaccine comprising the polypeptide, for example.

8 Claims, 2 Drawing Sheets
Specification includes a Sequence Listing.

(56) References Cited

OTHER PUBLICATIONS

Chedid et al. "Protective Effect of Delipidated Mycobacterial Cells and Purified Cell Walls against Ehrlich Carcinoma and a Syngeneic Lymphoid Leukemia in Mice," Cancer Res., Sep. 1973, 33:2187-2195.
Chen et al., "An EGF-like Protein a Complex with PfRh5 and Is Required for Invasion of Human Erythrocytes by Plasmodium falciparim," PLoS Pathogens, Sep. 2011, 7(9):1-19.
DDBJ.NIG.AC.JP/index-e.html [online], "Bioinformation and DDBJ Center," Apr. 2019, received on Aug. 15, 2019, retrieved from URL <https://www.ddbj.nig.ac.jp/index-e.html>, 1 page.
Erickson et al., "Cell-free translation of messenger RNA in a wheat germ system," Biomembranes Part J: Membrane Biogenesis: Assembly and Targeting, General Methods, Eukaryotes, 1983, 96:38-50.
Grupta et al., "Biodegradable polymer microspheres as vaccine adjuvants and delivery systems," Dev Biol Stand, 1998, 92:63-78.
Hall et al. "Sequence of Plasmodium falciparum Chromosomes 1, 3-9 and 13," Nature, Oct. 3, 2002, 419(6906):527-531.
Ito et al., "RALP1 Is a Rhoptry Neck Erythrocyte-Binding Protein of Plasmodium falciparum Merozoites and a Potential Blood-Stage Vaccine Candidate Antigen," Infection and Immunity, Nov. 2013, 81(11):4290-4298.
Johansen et al. "Revisiting PLA/PLGA microspheres: an analysis of their potential in parenteral vaccination," Eur. J Pharm Biopharm, Jul. 2000, 50(1):129-46.
Johnston et al., "Mass Isolation of Viable Wheat Embryos," Nature, 1957, 179(4551):160-161.
Nagaoka et al. "Abstract of the ASTMH 66th Annual Meeting: 423—Truncation of PfRipr Reveals Region That Induces Antibody with the Most Potent Growth Inhibitory Activity Against Plasmodiuim falciparum," Poster Session A, presented at ASTMH 66th Annual Meeting, Baltimore, MA, Nov. 5-9, 2017, Session 28, 1 page.
NCBI.com [online], "National Center for Biotechnology Information, NCBI Reference Sequence XM_001351269," Retrieved Aug. 15, 2019, retrieved from URL<https://www.ncbi.nlm.nih.gov/, 1 page.
"IUPAC-IUB Joint Commission on Biochemical Nomenclature (JCBN). Nomenclature and symbolism for amino acids and peptides. Recommendations 1983," European Journal of Biochemistry, 1984, 138(1):9-37., 29 pages.
Ntege et al. "Identification of Plasmodium Falciparum Reticulocyte Binding Protein Homologue 5-Interacting Protein, PfRipr, as a Highly Conserved Blood-Stage Malaria Vaccine Candidate," Vaccine, Nov. 2016, 34:5612-5622.
PCT International Preliminary Report on Patentability in International Appln. No. PCTJP2017040532, dated May 14, 2019, 12 pages.
PCT International Search Report and Written Opinion in International Appln. PCTJP2017040532, dated Feb. 13, 2018, 3 pages.
Plasmodb.org [online], "Plasmodium Genomics Resource, Gene Code PF3D7_0323400," Retrieved Aug. 15, 2019, Retrieved from URL <https://plasmodb.org/plasmo/>, 1 page.
Reed et al., "Key roles of adjuvants in modern vaccines," Nature Medicine, 2013, 19(12):1597-1608.
Thomspon et al. "Clustal W: Improving the Sensitivity of Progressive Multiple Sequence Alignment Through Sequence Weighting, Position-Specific Gap Penalties and Weight Matrix Choice," Nucleic Acid Res., Sep. 1994, 22(22):4673-4680.
Yamawaki et al. "Antitumor activity of squalene-treated cell-wall skeleton of Nocardia rubra in mice," Gan., 1978, 619-626 (English abstract).
Zbar et al. "Tumor Suppression by Cell Walls of *Mycobacterium bovis* Attached to Oil Droplets," JNCI: Journal of the National Cancer Institute, 1972, 48(3):831-835.
Douglas et al., "A defined mechanistic correlate of protection against Plasmodium falciparum malaria in non-human primates," Nature Communications, Apr. 2019, 10:1953, 8 pages.
Spring et al., "Phase 1/2a study of the malaria vaccine candidate apical membrane antigen-1 (AMA-1) administered in adjuvant system AS01B or AS02A," PLoS One, Apr. 2009 4(4):e5254, 13 pages.
Chiu et al., "Association of antibodies to Plasmodium falciparum reticulocyte binding protein homolog 5 with protection from clinical malaria," Frontiers in Microbiology, Jun. 2014, 5(314):1-8.
Reddy et al., "Multiprotein complex between the GPI-anchored CyRPA with PfRH5 and PfRipr is crucial for Plasmodium falciparum erythrocyte invasion," Proceedings of the National Academy of Sciences, Jan. 2015, 112(4):1179-1184, Supporting Information 1-7.

\* cited by examiner

```
SEQUENCE LISTING

<160> NUMBER OF SEQ ID NOS: 10

<210> SEQ ID NO 1
<211> LENGTH: 3261
<212> TYPE: DNA
<213> ORGANISM: Plasmodium falciparum

<400> SEQUENCE: 1
atgttcagaa ttttttttac ccttcttata ataatattaa tcaagaaaac atcggcaatt      60
gatttaatag aaggaatttt ttatgaaaaa aatgaaatag ataaattaac attttctctc     120
gatcatagag ttagagataa tttaaaaaca gatttgattt taaataataa tggggaaaat     180
gattatgctt atttaaacaa atacgtttat actatattaa atcgtgattc aacagaaaaa     240
attaaaacat ttttttctca taataaagac atgaaatcat gtgattattt tatatcaaaa     300
gaatataatt caagtgataa aacaaatcaa atatgttata aaaaaacatt ttgcggagta     360
gtaataccaa atagtgaaga aataaaaaca aataaaataa caaatgacaa actttattgt     420
gcacatttca attctacaca tataatcatt tattacatat cacaaccact tttattagaa     480
cctcatgttg tttatgaaga aacattttt gaaaaggaa aaaatgatca aattaattgc      540
caaggtatgt atatatctct aagatctgta catgtacata cacacaatgc tatattacaa     600
caagaaacac ttacatatat taaaaattta tgtgacggaa aaaacaattg taaattcgat     660
tttgattcaa taaaatatga aaataaatca cttactcatt atttgttttt tattaatata     720
caatatcaat gcataagtcc tctgaatcta caggaaaatg aaatgtgtga cgtatataat     780
gatgatacac ataaagcaac atgcaaatat ggttttaata aaatagaatt attaaaaaat     840
gtttgtgaag aaaattatag atgtacacaa gatatatgtt cagtaaatca attttgtgac     900
ggagaaaatg aaacatgtac atgcaaaaca tcattattac catcagctaa aaacaattgt     960
gaatacaacg atttatgtac agtttaaat tgtcctgaaa attccacatg tgaacaaata    1020
ggaaatggga aaaagctga atgtaaatgt gaaatggta aatattatca caataataaa    1080
tgttatacaa aaaatgattt agaattagcc ataaaaatag aaccacataa aaaagaaaaa    1140
ttttataaaa ataatttata tcaaggaaaa gcattaaaac cagaatatat ttttatgcaa    1200
tgtgaaaatg ggtctctat agaagttatt aatgcatatg tatcatgtta tagagtttca    1260
ttcaatctaa acaaattgaa atatgttaca gaatcattaa aaaaaatgtg tgatgggaaa    1320
```

| | | |
|---|---|---|
| accaaatgtg cttatggaaa tacaatagat ccaatagatg atttaaatca tcataatata | 1380 | |
| tgtaataatt ttaatacaat atttaaatat gattatttat gtgtattcaa taatcaaaat | 1440 | |
| attacttcag ataagaattc acatcttcat tctaatatac catcattata taattcaagt | 1500 | |
| attctaccag atattaataa atctaaattc catttgattt caagaaatag tcgaaccaac | 1560 | |
| caatatcctc ataacaatat atccatgcta gaaatacaaa atgaaatatc ctcacacaat | 1620 | |
| tcaaatcagt ttagtacaga tccacacaca aatagtaata atataaacaa tatgaatatt | 1680 | |
| aaaaaggtag aaatcttcag aagtcgtttt tcaagtaaat tacaatgtca agggggaaaa | 1740 | |
| ataaatattg ataaagcaat tttaaaaggt ggggaaggat gtaatgattt gcttttgacg | 1800 | |
| aattctttaa aatcatattg taatgattta tcagaatgtg atattggttt aatataccat | 1860 | |
| tttgatactt attgtattaa tgatcaatat cttttttgtat cttacagctg ctccaattta | 1920 | |
| tgtaataaat gtcataacaa ttctacatgc tatgggaaca gatttaatta tgattgtttt | 1980 | |
| tgtgataatc cttatatttc aaaatatgga aataaaattat gtgaacgtcc aaatgattgt | 2040 | |
| gaatctgttt tgtgttcaca aaatcaagtt tgtcaaattc ttccaaatga taattaata | 2100 | |
| tgtcaatgtg aagaaggata taaaaatgtt aaggtaaat gtgttccaga caacaaatgt | 2160 | |
| gatctttcat gcccatcaaa caaagtttgt gttatcgaaa atggaaaaca acatgtaaaa | 2220 | |
| tgttcagaac gttttgttct agagaatggt gtgtgtatat gtgctaatga ttataaaatg | 2280 | |
| gaagatggta ttaattgtat agccaaaaat aaatgtaaaa gaaaagaata tgaaaatatt | 2340 | |
| tgtacaaatc caaatgaaat gtgtgcttat aatgaagaaa cagatattgt aaaaatgtgaa | 2400 | |
| tgtaaagaac attattatag atcatcaaga ggtgaatgta tattaaatga ttattgtaaa | 2460 | |
| gatattaatt gtaaagaaaa tgaagaatgt tctattgtaa actttaaacc agaatgtgta | 2520 | |
| tgtaaagaaa atcttaaaaa aaataataaa ggagaatgta tttatgaaaa ctcctgttta | 2580 | |
| attaatgaag ggaattgtcc aaaagattca aatgtatttt atagagaata taaaccacat | 2640 | |
| gaatgtgtat gtaataaaca aggtcatgta gctgtcaatg gaaatgtgt tttagaagat | 2700 | |
| aaatgtgtac ataataaaaa atgttcagaa aattctatat gtgtaaatgt aatgaataaa | 2760 | |
| gaaccaatat gtgtatgtac atataattat tataaaaaag atggtgtatg tttaatacaa | 2820 | |
| aacccttgtc taaaagataa tggaggctgc tctagaaatt cagagtgtac atttaaatat | 2880 | |
| agtaaaatta attgtacatg taaagaaaat tataaaaata aagatgattc ttgtgtacct | 2940 | |
| aatacaaatg agtatgatga agttttaca ttccaatata atgacgatgc atctattatt | 3000 | |
| cttggagcat gtggtatgat cgaattttca tatatatata accaaattat ttggaaaata | 3060 | |
| aataactcaa aagaatctta cgtattttat tatgattatc caacagcagg taatatagaa | 3120 | |
| gttcaaatta aaaatgaaat atttcacact attatatatt tgaaaaaaaa aataggcaat | 3180 | |
| agtgttatct atgatgattt ccaagtagat catcaaacat gtatatatga aaatgtattt | 3240 | |
| tattatagta atcagaatta g | 3261 | |

<210> SEQ ID NO 2
<211> LENGTH: 1086
<212> TYPE: PRT
<213> ORGANISM: Plasmodium falciparum

<400> SEQUENCE: 2

Met Phe Arg Ile Phe Phe Thr Leu Leu Ile Ile Ile Leu Ile Lys Lys
1               5                   10                  15

Thr Ser Ala Ile Asp Leu Ile Glu Gly Ile Phe Tyr Glu Lys Asn Glu
            20                  25                  30

```
Ile Asp Lys Leu Thr Phe Ser Leu Asp His Arg Val Arg Asp Asn Leu
         35                  40                  45

Lys Thr Asp Leu Ile Leu Asn Asn Asn Gly Glu Asn Asp Tyr Ala Tyr
     50                  55                  60

Leu Asn Lys Tyr Val Tyr Thr Ile Leu Asn Arg Asp Ser Thr Glu Lys
 65                  70                  75                  80

Ile Lys Thr Phe Phe Ser His Asn Lys Asp Met Lys Ser Cys Asp Tyr
                     85                  90                  95

Phe Ile Ser Lys Glu Tyr Asn Ser Ser Asp Lys Thr Asn Gln Ile Cys
                100                 105                 110

Tyr Lys Lys Thr Phe Cys Gly Val Val Ile Pro Asn Ser Glu Glu Ile
                115                 120                 125

Lys Thr Asn Lys Ile Thr Asn Asp Lys Leu Tyr Cys Ala His Phe Asn
        130                 135                 140

Ser Thr His Ile Ile Ile Tyr Tyr Ile Ser Gln Pro Leu Leu Leu Glu
145                 150                 155                 160

Pro His Val Val Tyr Glu Glu Thr Phe Phe Glu Lys Gly Lys Asn Asp
                    165                 170                 175

Gln Ile Asn Cys Gln Gly Met Tyr Ile Ser Leu Arg Ser Val His Val
                180                 185                 190

His Thr His Asn Ala Ile Leu Gln Gln Glu Thr Leu Thr Tyr Ile Lys
                195                 200                 205

Asn Leu Cys Asp Gly Lys Asn Asn Cys Lys Phe Asp Phe Asp Ser Ile
        210                 215                 220

Lys Tyr Glu Asn Lys Ser Leu Thr His Tyr Leu Phe Phe Ile Asn Ile
225                 230                 235                 240

Gln Tyr Gln Cys Ile Ser Pro Leu Asn Leu Gln Glu Asn Glu Met Cys
                    245                 250                 255

Asp Val Tyr Asn Asp Asp Thr His Lys Ala Thr Cys Lys Tyr Gly Phe
                260                 265                 270

Asn Lys Ile Glu Leu Leu Lys Asn Val Cys Glu Glu Asn Tyr Arg Cys
        275                 280                 285

Thr Gln Asp Ile Cys Ser Val Asn Gln Phe Cys Asp Gly Glu Asn Glu
    290                 295                 300

Thr Cys Thr Cys Lys Thr Ser Leu Leu Pro Ser Ala Lys Asn Asn Cys
305                 310                 315                 320

Glu Tyr Asn Asp Leu Cys Thr Val Leu Asn Cys Pro Glu Asn Ser Thr
                325                 330                 335

Cys Glu Gln Ile Gly Asn Gly Lys Lys Ala Glu Cys Lys Cys Glu Asn
                340                 345                 350

Gly Lys Tyr Tyr His Asn Asn Lys Cys Tyr Thr Lys Asn Asp Leu Glu
            355                 360                 365

Leu Ala Ile Lys Ile Glu Pro His Lys Lys Glu Lys Phe Tyr Lys Asn
    370                 375                 380

Asn Leu Tyr Gln Gly Lys Ala Leu Lys Pro Glu Tyr Ile Phe Met Gln
385                 390                 395                 400

Cys Glu Asn Gly Phe Ser Ile Glu Val Ile Asn Ala Tyr Val Ser Cys
                405                 410                 415

Tyr Arg Val Ser Phe Asn Leu Asn Lys Leu Lys Tyr Val Thr Glu Ser
                420                 425                 430

Leu Lys Lys Met Cys Asp Gly Lys Thr Lys Cys Ala Tyr Gly Asn Thr
            435                 440                 445
```

```
Ile Asp Pro Ile Asp Asp Leu Asn His His Asn Ile Cys Asn Asn Phe
    450                 455                 460

Asn Thr Ile Phe Lys Tyr Asp Tyr Leu Cys Val Phe Asn Asn Gln Asn
465                 470                 475                 480

Ile Thr Ser Asp Lys Asn Ser His Leu His Ser Asn Ile Pro Ser Leu
                485                 490                 495

Tyr Asn Ser Ser Ile Leu Pro Asp Ile Asn Lys Ser Lys Phe His Leu
            500                 505                 510

Ile Ser Arg Asn Ser Arg Thr Asn Gln Tyr Pro His Asn Asn Ile Ser
        515                 520                 525

Met Leu Glu Ile Gln Asn Glu Ile Ser Ser His Asn Ser Asn Gln Phe
530                 535                 540

Ser Thr Asp Pro His Thr Asn Ser Asn Asn Ile Asn Asn Met Asn Ile
545                 550                 555                 560

Lys Lys Val Glu Ile Phe Arg Ser Arg Phe Ser Ser Lys Leu Gln Cys
                565                 570                 575

Gln Gly Gly Lys Ile Asn Ile Asp Lys Ala Ile Leu Lys Gly Gly Glu
            580                 585                 590

Gly Cys Asn Asp Leu Leu Leu Thr Asn Ser Leu Lys Ser Tyr Cys Asn
        595                 600                 605

Asp Leu Ser Glu Cys Asp Ile Gly Leu Ile Tyr His Phe Asp Thr Tyr
    610                 615                 620

Cys Ile Asn Asp Gln Tyr Leu Phe Val Ser Tyr Ser Cys Ser Asn Leu
625                 630                 635                 640

Cys Asn Lys Cys His Asn Asn Ser Thr Cys Tyr Gly Asn Arg Phe Asn
                645                 650                 655

Tyr Asp Cys Phe Cys Asp Asn Pro Tyr Ile Ser Lys Tyr Gly Asn Lys
            660                 665                 670

Leu Cys Glu Arg Pro Asn Asp Cys Glu Ser Val Leu Cys Ser Gln Asn
        675                 680                 685

Gln Val Cys Gln Ile Leu Pro Asn Asp Lys Leu Ile Cys Gln Cys Glu
    690                 695                 700

Glu Gly Tyr Lys Asn Val Lys Gly Lys Cys Val Pro Asp Asn Lys Cys
705                 710                 715                 720

Asp Leu Ser Cys Pro Ser Asn Lys Val Cys Val Ile Glu Asn Gly Lys
                725                 730                 735

Gln Thr Cys Lys Cys Ser Glu Arg Phe Val Leu Glu Asn Gly Val Cys
            740                 745                 750

Ile Cys Ala Asn Asp Tyr Lys Met Glu Asp Gly Ile Asn Cys Ile Ala
        755                 760                 765

Lys Asn Lys Cys Lys Arg Lys Glu Tyr Glu Asn Ile Cys Thr Asn Pro
    770                 775                 780

Asn Glu Met Cys Ala Tyr Asn Glu Glu Thr Asp Ile Val Lys Cys Glu
785                 790                 795                 800

Cys Lys Glu His Tyr Tyr Arg Ser Ser Arg Gly Glu Cys Ile Leu Asn
                805                 810                 815

Asp Tyr Cys Lys Asp Ile Asn Cys Lys Glu Asn Glu Cys Ser Ile
            820                 825                 830

Val Asn Phe Lys Pro Glu Cys Val Cys Lys Glu Asn Leu Lys Lys Asn
        835                 840                 845

Asn Lys Gly Glu Cys Ile Tyr Glu Asn Ser Cys Leu Ile Asn Glu Gly
    850                 855                 860

Asn Cys Pro Lys Asp Ser Lys Cys Ile Tyr Arg Glu Tyr Lys Pro His
```

```
                865                 870                 875                 880
            Glu Cys Val Cys Asn Lys Gln Gly His Val Ala Val Asn Gly Lys Cys
                            885                 890                 895
            Val Leu Glu Asp Lys Cys Val His Asn Lys Lys Cys Ser Glu Asn Ser
                        900                 905                 910
            Ile Cys Val Asn Val Met Asn Lys Glu Pro Ile Cys Val Cys Thr Tyr
                    915                 920                 925
            Asn Tyr Tyr Lys Lys Asp Gly Val Cys Leu Ile Gln Asn Pro Cys Leu
                930                 935                 940
            Lys Asp Asn Gly Gly Cys Ser Arg Asn Ser Glu Cys Thr Phe Lys Tyr
            945                 950                 955                 960
            Ser Lys Ile Asn Cys Thr Cys Lys Glu Asn Tyr Lys Asn Lys Asp Asp
                            965                 970                 975
            Ser Cys Val Pro Asn Thr Asn Glu Tyr Asp Ser Phe Thr Phe Gln
                        980                 985                 990
            Tyr Asn Asp Asp Ala Ser Ile Ile Leu Gly Ala Cys Gly Met Ile Glu
                    995                 1000                1005
            Phe Ser Tyr Ile Tyr Asn Gln Ile Ile Trp Lys Ile Asn Asn Ser
                1010                1015                1020
            Lys Glu Ser Tyr Val Phe Tyr Tyr Asp Tyr Pro Thr Ala Gly Asn
                1025                1030                1035
            Ile Glu Val Gln Ile Lys Asn Glu Ile Phe His Thr Ile Ile Tyr
                1040                1045                1050
            Leu Lys Lys Lys Ile Gly Asn Ser Val Ile Tyr Asp Asp Phe Gln
                1055                1060                1065
            Val Asp His Gln Thr Cys Ile Tyr Glu Asn Val Phe Tyr Tyr Ser
                1070                1075                1080
            Asn Gln Asn
                1085

<210> SEQ ID NO 3
<211> LENGTH: 645
<212> TYPE: DNA
<213> ORGANISM: Artificial Sequence
<220> FEATURE:
<223> OTHER INFORMATION: Nucleotide sequence encoding the amino acid
      sequence at positions 720-934 of SEQ ID NO: 2

<400> SEQUENCE: 3
tgtgatcttt catgcccatc aaacaaagtt tgtgttatcg aaaatggaaa acaaacatgt       60
aaatgttcag aacgttttgt tctagagaat ggtgtgtgta tatgtgctaa tgattataaa      120
atggaagatg gtattaattg tatagccaaa aataaatgta aagaaaaga  atatgaaaat      180 atttgtacaa atccaaatga atgtgtgct  tataatgaag aaacagatat tgtaaaatgt      240
gaatgtaaag aacattatta tagatcatca agaggtgaat gtatattaaa tgattattgt      300
aaagatatta ttgtaaaga  aaatgaagaa tgttctattg taaactttaa accagaatgt      360
gtatgtaaag aaaatcttaa aaaaaataat aaaggagaat gtatttatga aaactcctgt      420
ttaattaatg aagggaattg tccaaaagat tcaaaatgta tttatagaga atataaacca      480
catgaatgtg tatgtaataa acaaggtcat gtagctgtca atggaaaatg tgttttagaa      540
gataaatgtg tacataataa aaaatgttca gaaaattcta tatgtgtaaa tgtaatgaat      600
aaagaaccaa tatgtgtatg tacatataat tattataaaa aagat                     645

<210> SEQ ID NO 4
```

<211> LENGTH: 215
<212> TYPE: PRT
<213> ORGANISM: Artificial Sequence
<220> FEATURE:
<223> OTHER INFORMATION: Amino acid sequence at positions 720-934 of SEQ
      ID NO: 2

<400> SEQUENCE: 4

```
Cys Asp Leu Ser Cys Pro Ser Asn Lys Val Cys Val Ile Glu Asn Gly
1               5                   10                  15

Lys Gln Thr Cys Lys Cys Ser Glu Arg Phe Val Leu Glu Asn Gly Val
            20                  25                  30

Cys Ile Cys Ala Asn Asp Tyr Lys Met Glu Asp Gly Ile Asn Cys Ile
        35                  40                  45

Ala Lys Asn Lys Cys Lys Arg Lys Glu Tyr Glu Asn Ile Cys Thr Asn
    50                  55                  60

Pro Asn Glu Met Cys Ala Tyr Asn Glu Glu Thr Asp Ile Val Lys Cys
65                  70                  75                  80

Glu Cys Lys Glu His Tyr Tyr Arg Ser Ser Arg Gly Glu Cys Ile Leu
                85                  90                  95

Asn Asp Tyr Cys Lys Asp Ile Asn Cys Lys Glu Asn Glu Cys Ser
            100                 105                 110

Ile Val Asn Phe Lys Pro Glu Cys Val Cys Lys Glu Asn Leu Lys Lys
        115                 120                 125

Asn Asn Lys Gly Glu Cys Ile Tyr Glu Asn Ser Cys Leu Ile Asn Glu
    130                 135                 140

Gly Asn Cys Pro Lys Asp Ser Lys Cys Ile Tyr Arg Glu Tyr Lys Pro
145                 150                 155                 160

His Glu Cys Val Cys Asn Lys Gln Gly His Val Ala Val Asn Gly Lys
                165                 170                 175

Cys Val Leu Glu Asp Lys Cys Val His Asn Lys Lys Cys Ser Glu Asn
            180                 185                 190

Ser Ile Cys Val Asn Val Met Asn Lys Glu Pro Ile Cys Val Cys Thr
        195                 200                 205

Tyr Asn Tyr Tyr Lys Lys Asp
    210                 215
```

<210> SEQ ID NO 5
<211> LENGTH: 3198
<212> TYPE: DNA
<213> ORGANISM: Artificial Sequence
<220> FEATURE:
<223> OTHER INFORMATION: Wheat codon-optimized sequence encoding the
      amino acid sequence at positions 21-1086 of SEQ ID NO: 2

<400> SEQUENCE: 5

```
gatctgatcg agggcatctt ctacgagaag aacgagatcg acaagctcac cttctccctg      60
gaccacaggg tccgcgataa cctcaagacg gacctcatcc tgaacaacaa cggcgagaac     120
gattacgcgt acctgaacaa gtatgtgtac accatcctca cagggactc aaccgagaag      180 atcaagacgt tcttctctca caacaaggat atgaagtctt gcgactactt catctccaag     240
gagtacaact ccagcgataa gaccaaccaa atctgctaca agaagacgtt ctgcggcgtg     300
gtcatcccaa actccgagga gatcaagacc aacaagatca cgaacgacaa gctctactgc     360
gcccatttca actccacccca catcatcatc tactacatca gccagccact cctgctggag     420
ccgcacgttg tgtacgagga gaccttcttc gagaagggca agaacgacca aatcaactgc     480
caggggatgt acatctcact gcggtctgtc cacgttcata cccacaacgc gatcctccaa     540
```

```
caggagaccc tgacgtacat caagaacctc tgcgacggca agaacaactg caagttcgac      600
ttcgatagca tcaagtacga gaacaagtcg ctcacccact acctgttctt catcaacatc      660
cagtaccagt gcatctcccc gctcaacctg caagagaacg agatgtgcga cgtctacaac      720
gacgatcccc acaaggccac gtgcaagtac ggcttcaaca agatcgagct gctcaagaac      780
gtctgcgagg agaactaccg ctgcacccaa gatatctgct ccgttaacca gttctgcgac      840
ggcgagaacg agacctgcac gtgcaagacg tcgctgctcc cctcagcgaa gaacaactgc      900
gagtacaacg acctctgcac cgtgctgaac tgccctgaga cagcacgtg cgagcagatc       960 ggcaacggga agaaggctga gtgcaagtgc gagaacggca agtactacca taacaacaag     1020
tgctacacca agaacgacct ggagctggcg atcaagatcg agccacacaa gaaggagaag     1080
ttctacaaga caacctcta ccaaggcaag gctctgaagc cggagtacat cttcatgcag      1140
tgcgagaacg ggttcagcat cgaggtcatc aacgcctacg tctcgtgcta ccgcgtttca     1200
ttcaacctca acaagctgaa gtatgtgacc gagtccctga agaagatgtg cgatggcaag     1260
accaagtgcg cgtacgggaa cacgatcgac ccaatcgacg atctcaacca ccataacatc     1320
tgcaacaact tcaacaccat cttcaagtac gattacctgt gcgtgttcaa caaccaaaac     1380
atcacgtctg acaagaactc ccatctccac agcaacatcc cctcgctcta caactcgtca     1440
atcctgcctg acatcaacaa gtcgaagttc catctgatct ccaggaacag ccgcaccaac     1500
cagtacccac acaacaacat ctccatgctg gagatccaaa cgagatctc ttcccataac      1560 tcaaaccagt tctctaccga cccgcacacg aacagcaaca acatcaacaa catgaacatc     1620
aagaaggtcg agatcttccg gtcgagattc agctcgaagc tgcaatgcca gggcgggaag     1680
atcaacatcg ataaggctat cctcaagggc ggggagggct gcaacgacct gctcctgacc     1740
aactcgctca gtcatactg caacgatctg agcgagtgcg acatcgggct catctaccat      1800
ttcgatacct actgcatcaa cgaccaatac ctgttcgtgt cctacagctg ctcgaacctc     1860
tgcaacaagt gccacaacaa ctccacctgc tacggcaaca ggttcaacta cgactgcttc     1920
tgcgataacc catacatcag caagtacggg aacaagctgt gcgagcgccc gaacgattgc     1980
gagtccgtgc tctgcagcca aaaccaggtc tgccaaatcc tcccaaacga caagctgatc     2040
tgccagtgcg aggaaggcta caagaacgtg aaggggaagt gcgtcccaga caacaagtgc     2100
gatctgtctt gcccgtccaa caaggtgtgc gtcatcgaga acggcaagca gacctgcaag     2160
tgcagcgagc ggttcgttct ggagaacggc gtgtgcatct gcgctaacga ttacaagatg     2220
gaggacggga tcaactgcat cgccaagaac aagtgcaaga gaaaggagta cgagaacatc     2280
tgcaccaacc ccaacgagat gtgcgcttac aacgaggaga cggacatcgt caagtgcgag     2340
tgcaaggagc actactaccg gtcatctaga ggcgagtgca tcctcaacga ctactgcaag     2400
gatatcaact gcaaggagaa cgaggagtgc tccatcgtta acttcaagcc tgagtgcgtg     2460
tgcaaggaga acctgaagaa gaacaacaag ggcgagtgca tctacgagaa ctcttgcctc     2520
atcaacgagg ggaactgccc caaggactcc aagtgcatct acaggagta caagcctcat      2580 gagtgcgtgt gcaacaagca aggccacgtt gccgtgaacg ggaagtgcgt cctggaggac     2640
aagtgcgttc acaacaagaa gtgcagcgag aactcgatcg cgtcaacgt tatgaacaag      2700 gagcccatct gcgtgtgcac ctacaactac tacaagaagg atggcgtctg cctcatccag     2760
aacccttgcc tgaaggacaa cggcgggtgc tcacgcaact ctgagtgcac cttcaagtac     2820
tcaaagatca actgcacgtg caaggagaac tacaagaaca aggacgattc ttgcgtgccc     2880
```

```
aacaccaacg agtacgacga gtcgttcacg ttccaataca acgacgatgc ctcaatcatc    2940
ctcggcgcgt gcgggatgat cgagttctcc tacatctaca accagatcat ctggaagatc    3000
aacaactcca aggagagcta cgttttctac tacgactacc cgaccgccgg caacatcgag    3060
gtgcaaatca agaacgagat cttccatacc atcatctacc tcaagaagaa gatcgggaac    3120
tcagtcatct acgacgattt ccaagttgac caccagacct gcatctacga gaacgtgttc    3180
tactactcca accagaac                                                  3198

<210> SEQ ID NO 6
<211> LENGTH: 645
<212> TYPE: DNA
<213> ORGANISM: Artificial Sequence
<220> FEATURE:
<223> OTHER INFORMATION: Wheat codon-optimized sequence encoding the
      amino acid sequence at positions 720-934 of SEQ ID NO: 2

<400> SEQUENCE: 6
tgcgatctgt cttgcccgtc caacaaggtg tgcgtcatcg agaacggcaa gcagacctgc      60
aagtgcagcg agcggttcgt tctggagaac ggcgtgtgca tctgcgctaa cgattacaag     120
atggaggacg ggatcaactg catcgccaag aacaagtgca agagaaagga gtacgagaac     180
atctgcacca accccaacga gatgtgcgct acaacgagg agacggacat cgtcaagtgc     240
gagtgcaagg agcactacta ccggtcatct agaggcgagt gcatcctcaa cgactactgc     300
aaggatatca actgcaagga gaacgaggag tgctccatcg ttaacttcaa gcctgagtgc     360
gtgtgcaagg agaacctgaa gaagaacaac aagggcgagt gcatctacga gaactcttgc     420
ctcatcaacg aggggaactg ccccaaggac tccaagtgca tctacaggga gtacaagcct     480
catgagtgcg tgtgcaacaa gcaaggccac gttgccgtga acgggaagtg cgtcctggag     540
gacaagtgcg ttcacaacaa gaagtgcagc gagaactcga tctgcgtcaa cgttatgaac     600
aaggagccca tctgcgtgtg cacctacaac tactacaaga aggat                    645

<210> SEQ ID NO 7
<211> LENGTH: 549
<212> TYPE: DNA
<213> ORGANISM: Artificial Sequence
<220> FEATURE:
<223> OTHER INFORMATION: Nucleotide sequence encoding the amino acid
      sequence at positions 648-830 of SEQ ID NO: 2

<400> SEQUENCE: 7
tctacatgct atgggaacag atttaattat gattgttttt gtgataatcc ttatatttca      60
aaatatggaa ataaattatg tgaacgtcca aatgattgtg aatctgtttt gtgttcacaa     120
aatcaagttt gtcaaattct tccaaatgat aaattaatat gtcaatgtga agaaggatat     180
aaaaatgtta aaggtaaatg tgttccagac aacaaatgtg atctttcatg cccatcaaac     240
aaagtttgtg ttatcgaaaa tggaaaacaa acatgtaaat gttcagaacg ttttgttcta     300
gagaatggtg tgtgtatatg tgctaatgat tataaaatgg aagatggtat taattgtata     360
gccaaaaata aatgtaaaag aaaagaatat gaaaatattt gtacaaatcc aaatgaaatg     420
tgtgcttata tgaagaaaac agatattgta aaatgtgaat gtaaagaaca ttattataga     480
tcatcaagag gtgaatgtat attaaatgat tatttgtaaag atattaattg taagaaaat     540 gaagaatgt                                                            549

<210> SEQ ID NO 8
<211> LENGTH: 183
```

<212> TYPE: PRT
<213> ORGANISM: Artificial Sequence
<220> FEATURE:
<223> OTHER INFORMATION: Amino acid sequence at positions 648-830 of SEQ
      ID NO: 2

<400> SEQUENCE: 8

```
Ser Thr Cys Tyr Gly Asn Arg Phe Asn Tyr Asp Cys Phe Cys Asp Asn
1               5                   10                  15

Pro Tyr Ile Ser Lys Tyr Gly Asn Lys Leu Cys Glu Arg Pro Asn Asp
            20                  25                  30

Cys Glu Ser Val Leu Cys Ser Gln Asn Gln Val Cys Gln Ile Leu Pro
        35                  40                  45

Asn Asp Lys Leu Ile Cys Gln Cys Glu Glu Gly Tyr Lys Asn Val Lys
    50                  55                  60

Gly Lys Cys Val Pro Asp Asn Lys Cys Asp Leu Ser Cys Pro Ser Asn
65                  70                  75                  80

Lys Val Cys Val Ile Glu Asn Gly Lys Gln Thr Cys Lys Cys Ser Glu
                85                  90                  95

Arg Phe Val Leu Glu Asn Gly Val Cys Ile Cys Ala Asn Asp Tyr Lys
            100                 105                 110

Met Glu Asp Gly Ile Asn Cys Ile Ala Lys Asn Lys Cys Lys Arg Lys
        115                 120                 125

Glu Tyr Glu Asn Ile Cys Thr Asn Pro Asn Glu Met Cys Ala Tyr Asn
    130                 135                 140

Glu Glu Thr Asp Ile Val Lys Cys Glu Cys Lys Glu His Tyr Tyr Arg
145                 150                 155                 160

Ser Ser Arg Gly Glu Cys Ile Leu Asn Asp Tyr Cys Lys Asp Ile Asn
                165                 170                 175

Cys Lys Glu Asn Glu Glu Cys
            180
```

<210> SEQ ID NO 9
<211> LENGTH: 549
<212> TYPE: DNA
<213> ORGANISM: Artificial Sequence
<220> FEATURE:
<223> OTHER INFORMATION: Wheat codon-optimized sequence encoding the
      amino acid sequence at positions 648-830 of SEQ ID NO: 2

<400> SEQUENCE: 9

```
tccacctgct acggcaacag gttcaactac gactgcttct gcgataaccc atacatcagc    60
aagtacggga caagctgtg cgagcgcccg aacgattgcg agtccgtgct ctgcagccaa   120
aaccaggtct gccaaatcct cccaaacgac aagctgatct gccagtgcga ggaaggctac   180
aagaacgtga aggggaagtg cgtcccagac aacaagtgcg atctgtcttg cccgtccaac   240
aaggtgtgcg tcatcgagaa cggcaagcag acctgcaagt gcagcgagcg gttcgttctg   300
gagaacggcg tgtgcatctg cgctaacgat tacaagatgg aggacgggat caactgcatc   360
gccaagaaca agtgcaagag aaaggagtac gagaacatct gcaccaaccc caacgagatg   420
tgcgcttaca cggaggagac ggacatcgtc aagtgcgagt gcaaggagca ctactaccgg   480
tcatctagag gcgagtgcat cctcaacgac tactgcaagg atatcaactg caaggagaac   540
gaggagtgc                                                           549
```

<210> SEQ ID NO 10
<211> LENGTH: 645
<212> TYPE: DNA

<213> ORGANISM: Artificial Sequence
<220> FEATURE:
<223> OTHER INFORMATION: Baculovirus codon-optimized sequence encoding
      the amino acid sequence at positions 720-934 of SEQ ID NO: 2

<400> SEQUENCE: 10

```
tgcgacttgt cttgtccctc aaacaaggtg tgcgtcatcg agaacggaaa gcagacctgc        60
aaatgttccg agaggttcgt gctggaaaac ggagtctgca tttgtgcaaa cgactacaag       120
atggaggatg gtatcaactg cattgccaag aacaagtgta agagaaaaga gtacgaaaac       180
atctgcacca acccaaacga aatgtgcgct tacaacgagg aaactgatat tgtgaagtgc       240
gagtgtaaag aacattacta ccgctccagc cgtggcgagt gcatcctcaa cgactactgc       300
aaggatatta actgtaaaga aaacgaggaa tgctctatcg tcaacttcaa gccggagtgc       360
gtttgtaagg aaaacctgaa gaaaacaac aagggcgagt gcatctacga aaactcctgt       420
ctcattaacg agggaaactg ccctaaggac agcaaatgta tctaccgcga gtacaagccc       480
cacgaatgcg tctgtaacaa gcaaggtcat gttgctgtga acggcaagtg cgttctggag       540
gataaatgtg tgcacaacaa gaaatgcagt gaaaactcga tctgtgtcaa cgttatgaac       600
aaggagccca tctgtgtctg cacctacaac tactacaaaa aggac                      645
```

MALARIA VACCINE

TECHNICAL FIELD

The present application claims priority to Japanese Patent Application Nos. 2016-220512 and 2017-161442, the whole of which is herein incorporated by reference.

The present invention relates to a vaccine antigen for use in the prevention of infection with a malaria parasite or in the prevention of development of malaria disease, for example.

BACKGROUND

Malaria, which is an infection of a parasitic protozoa of *Plasmodium* such as *Plasmodium falciparum*, is widespread in tropical and subtropical regions. Malaria infection develops when malaria parasites enter into human bodies by using Anopheles as vectors and proliferate through the sporozoite stage, liver stage, and red blood cell stage. In each stage, malaria parasites produce proteins in the human body. Vaccines that induce antibodies to such proteins are thus expected to attack malaria parasites, or suppress infection, or proliferation after the infection in the body, of malaria parasites. Although malaria vaccines have been studied or under development all over the world, no malaria vaccine has been used in clinical. Rh5 interacting protein (PlasmoDB gene code: PF3D7_0323400, http://plasmodb.org/), also called as Ripr, is one of proteins considered to be expressed in *Plasmodium falciparum* at the merozoite stage. Ripr is suggested to be an antigen for malaria vaccines (Non-Patent documents 1 and 2 and Patent documents 1 to 4).

CITATION LIST

Patent Documents

Patent Document 1: U.S. Patent Application Publication No. 2015/0366958
Patent Document 2: WO 2012/061882
Patent Document 3: WO 2015/144874
Patent Document 4: WO 2014/174054

Non Patent Documents

Non-Patent Document 1: Nature (London) (1999), 400 (6744), 532-538
Non-Patent Document 2: Nature (London, United Kingdom) (2002), 419 (6906), 527-531

SUMMARY

One of objects of the present invention is to provide a polypeptide useful as a malaria vaccine antigen.

Intensive studies of the present inventors have found that an antibody obtained with a fragment of Ripr, a protein from a malaria parasite, as an antigen inhibits growth of malaria parasites, and the present invention has been achieved. That is, the present invention relates to:

[1] A polypeptide consisting of an amino acid sequence selected from:
(a) the amino acid sequence of SEQ ID NO: 4 or SEQ ID NO: 8,
(b) an amino acid sequence that differs from the amino acid sequence of SEQ ID NO: 4 or SEQ ID NO: 8 by substitution, deletion, addition, or insertion of 1 to 10 amino acid residues, preferably 1-5 amino acid residues, more preferably 1, 2 or 3 amino acid residues, and
(c) an amino acid sequence that has at least 95%, preferably 97%, more preferably 99% sequence identity with the amino acid sequence of SEQ ID NO: 4 or SEQ ID NO: 8.

[2] A polypeptide comprising the polypeptide according to item 1 and a carrier attached thereto.

[3] The polypeptide according to item 2, wherein the carrier is a viral particle, a lipid particle, or a carrier protein.

[4] The polypeptide according to any one of items 1 to 3, wherein the polypeptide is for use as a malaria vaccine antigen.

[5] A malaria vaccine comprising the polypeptide according to any one of items 1 to 4.

[6] The malaria vaccine according to item 5, wherein the malaria vaccine further comprises, or is administered in combination with, at least one malaria vaccine antigen selected from CSP, TRAP, MSP1, AMA-1, SERA5, GAMA, EBA175, RH5, Pfs25 or Pfs230.

[7] The malaria vaccine according to item 5 or 6, wherein the malaria vaccine further comprises, or is administered in combination with, a vaccine antigen against at least one infectious disease selected from polio, diphtheria, pertussis or tetanus.

[8] The malaria vaccine according to any one of items 5 to 7, wherein the malaria vaccine is for use in the prevention of infection with a malaria parasite, for use in the prevention of development of malaria disease after infection with a malaria parasite, or for use in the treatment of malaria disease.

[9] A polynucleotide consisting of a nucleotide sequence encoding the polypeptide according to item 1.

[10] A polynucleotide comprising the polynucleotide according to item 9 and a promoter and/or a regulatory element connected thereto that enables expression of the polynucleotide according to item 9 in a host cell.

[11] An expression vector comprising the polynucleotide according to item 9 or 10.

[12] A malaria vaccine comprising the polynucleotide according to item 9 or 10 or the expression vector according to item 11.

[13] A recombinant host cell transformed with the vector according to item 11.

[14] The recombinant host cell according to item 13, wherein the cell is a bacterium cell, a yeast cell, an insect cell or a mammalian cell.

[15] An antibody that specifically recognizes the polypeptide according to item 1.

[16] A pharmaceutical composition comprising the polypeptide according to any one of items 1 to 4, the polynucleotide according to item 9 or 10, the expression vector according to item 11, or the antibody according to item 15 as an active ingredient.

The present invention provides a polypeptide useful as a malaria vaccine antigen and a malaria vaccine comprising the polypeptide, for example.

DESCRIPTION OF EMBODIMENTS

1. Definitions

Figure 1:
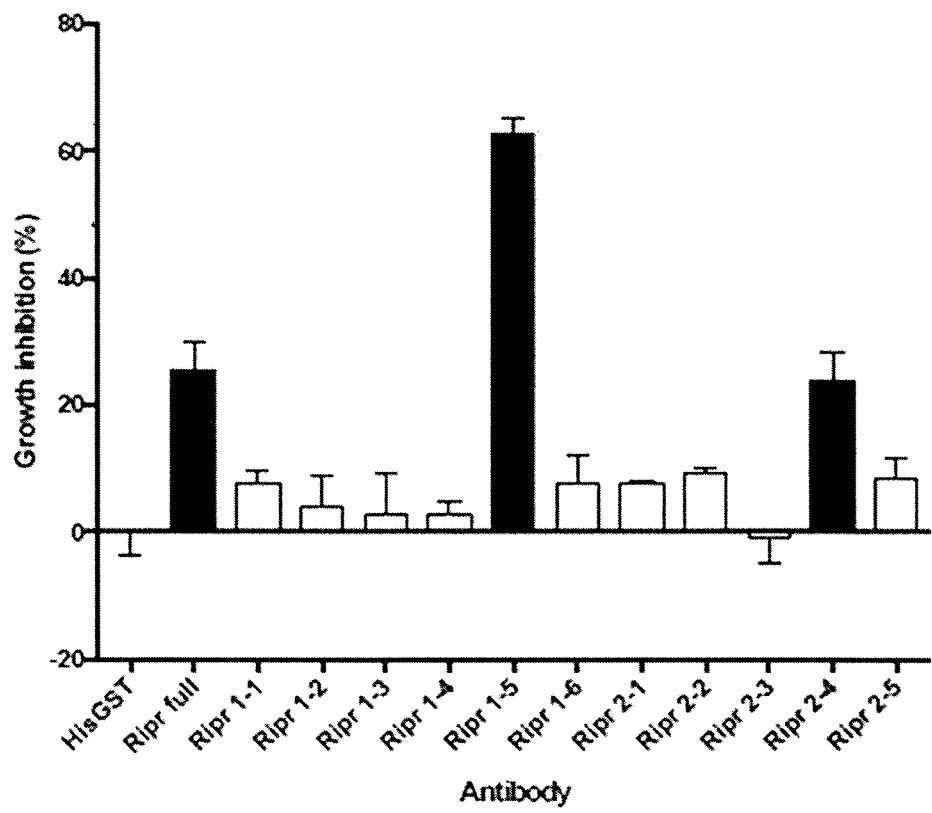
FIG. 1 shows the rate of growth inhibition of malaria parasites with a polyclonal IgG antibody obtained by immunization of a rabbit with Ripr or a fragment of Ripr produced in a wheat germ cell-free protein expression system.

Abbreviations used in description of an amino acid, a (poly)peptide, or a (poly)nucleotide have meaning as defined in IUPAC-IUB Communication on Biological Nomenclature, Eur. J. Biochem., 138:9(1984), or the "Guidelines for the preparation of the description comprising amino acid sequence or nucleotide sequence" of JPO, or as conventionally used in this technical field.

As used herein, the term "Rh5 interacting protein" (or "Ripr") refers to a protein considered to be expressed in *Plasmodium falciparum* at the merozoite stage, and includes a protein comprising the amino acid sequence of SEQ ID NO: 2, which corresponds to PlasmoDB gene code: PF3D7_0323400 (http://plasmodb.org/), or NCBI Reference Sequence: XP_001351305 (https://www.ncbi.nlm.nih.gov/), and a protein comprising an amino acid sequence substantially the same as SEQ ID NO: 2.

The "amino acid sequence substantially the same as SEQ ID NO: 2" includes:
(a) an amino acid sequence that differs from the amino acid sequence of SEQ ID NO: 2 by substitution, deletion, addition, or insertion of 1 to 10 amino acid residues, preferably 1-5 amino acid residues, more preferably 1, 2 or 3 amino acid residues, and
(b) an amino acid sequence that has at least 95%, preferably at least 97%, or more preferably at least 99% sequence identity with the amino acid sequence of SEQ ID NO: 2.

As used herein, the term "Ripr gene" refers to any Ripr-encoding polynucleotide which may be DNA or RNA. Specific examples of the Ripr gene include a polynucleotide having the nucleotide sequence of SEQ ID NO: 1, which corresponds to PlasmoDB gene code: PF3D7_0323400 (http://plasmodb.org/), or NCBI Reference Sequence: XM_001351269 (https://www.ncbi.nlm.nih.gov/).

As used herein, the term "sequence identity" refers to amino acid sequence identity between two proteins. The "sequence identity" is determined by comparison of optimally aligned two amino acid sequences. Amino acid addition or amino acid deletion (or a gap) may be found in an amino acid sequence compared with another amino acid sequence optimally aligned thereto. The sequence identity can be quantified, for example through alignment of amino acid sequences in accordance with Clustal W algorism by the use of Vector NTI (Nucleic Acid Res., 22(22):4673-4680 (1994)). Software useful for determination of the "sequence identity" includes a software for sequence analysis such as Vector NTI, or GENETYX-MAC, or other tool for sequence analysis available from a public database, for example at http://www.ddbj.nig.ac.jp.

2. Polypeptide

The present invention relates to a peptide fragment useful as a malaria vaccine antigen, wherein the peptide fragment consists of part of an amino acid sequence of Ripr. More specifically, the peptide fragment of the present invention, hereinafter also referred to as "polypeptide of the present invention", may be a polypeptide consisting of the amino acid sequence of SEQ ID NO: 4 which corresponds to the amino acid sequence at positions 720 to 934 of SEQ ID NO: 2, or the amino acid sequence of SEQ ID NO: 8 which corresponds to the amino acid sequence at positions 648 to 830 of SEQ ID NO: 2, or a polypeptide consisting of an amino acid sequence substantially the same as SEQ ID NO: 4 or SEQ ID NO: 8.

The amino acid sequence substantially the same as SEQ ID NO: 4 or SEQ ID NO: 8 includes:
(a) an amino acid sequence that differs from the amino acid sequence of SEQ ID NO: 4 or 8 by substitution, deletion, addition, or insertion of 1 to 10 amino acid residues, preferably 1-5 amino acid residues, more preferably 1, 2 or 3 amino acid residues, and
(b) an amino acid sequence that has at least 95%, preferably at least 97%, or more preferably at least 99% sequence identity with the amino acid sequence of SEQ ID NO: 4 or SEQ ID NO: 8.

The number of amino acid residue modification and the position(s) of modified amino acid residue(s) in a polypeptide of the present invention compared with the original amino acid sequence are selected appropriately, so that the polypeptide has an immunological activity equivalent to that of the original polypeptide. For preparing such a polypeptide, specific type(s) or position(s) of amino acid(s) to be substituted, deleted, added or inserted can be determined by a well-known computer program such as DNA Star software. Typically, not more than 5%, preferably not more than 3%, or more preferably not more than 1% of amino acid residues in the original polypeptide may be modified. When a polypeptide is altered by amino acid substitution, a substitute amino acid can be selected appropriately so that the altered polypeptide has an immunological activity equivalent to that of the polypeptide of the original amino acid sequence. For maintaining characteristics of the original protein, a substitute amino acid is preferably selected from amino acids having similar polarity, electricity, solubility, hydrophobicity, amphiphilicity, or other property to an original amino acid. For example, amino acid substitution may be made between amino acids belonging to a group of non-polar amino acids, such as Ala, Val, Leu, Ile, Pro, Met, Phe and Trp, amino acids belonging to a group of uncharged amino acids, such as Gly, Ser, Thr, Cys, Tyr, Asn and Gln, amino acids belonging to a group of acidic amino acids, such as Asp and Glu, or amino acids belonging to a group of basic amino acids, such as Lys, Arg and His.

Therefore, in a preferred embodiment, the polypeptide of the present invention is selected from:
(a) a polypeptide consisting of the amino acid sequence of SEQ ID NO: 4 or SEQ ID NO: 8,
(b) a polypeptide consisting of an amino acid sequence that differs from the amino acid sequence of SEQ ID NO: 4 or 8 by substitution, deletion, addition, or insertion of 1 to 10 amino acid residues, preferably 1-5 amino acid residues, more preferably 1, 2 or 3 amino acid residues, wherein the polypeptide has an immunological activity equivalent to that of the corresponding polypeptide consisting of the amino acid sequence of SEQ ID NO: 4 or SEQ ID NO: 8, or
(c) a polypeptide consisting of an amino acid sequence that has at least 95%, preferably at least 97%, or more preferably at least 99% sequence identity with the amino acid sequence of SEQ ID NO: 4 or SEQ ID NO: 8, wherein the polypeptide has an immunological activity equivalent to that of the corresponding polypeptide consisting of the amino acid sequence of SEQ ID NO: 4 or SEQ ID NO: 8.

More preferably, the polypeptide of the present invention is selected from:
(a) a polypeptide consisting of the amino acid sequence of SEQ ID NO: 4,
(b) a polypeptide consisting of an amino acid sequence that differs from the amino acid sequence of SEQ ID NO: 4 by substitution, deletion, addition, or insertion of 1 to 10 amino acid residues, preferably 1-5 amino acid residues, more preferably 1, 2 or 3 amino acid residues, wherein the polypeptide has an immunological activity equivalent to that of the polypeptide consisting of the amino acid sequence of SEQ ID NO: 4, or
(c) a polypeptide consisting of an amino acid sequence that has at least 95%, preferably at least 97%, or more preferably at least 99% sequence identity with the amino acid sequence of SEQ ID NO: 4, wherein the polypeptide has an immunological activity equivalent to that of the polypeptide consisting of the amino acid sequence of SEQ ID NO: 4.

The term "immunological activity" as used herein in the context as "an immunological activity equivalent to that of a polypeptide consisting of the amino acid sequence of SEQ ID NO: X" (wherein X is an integer) refers to an activity to induce immune response to a malaria parasite. A polypeptide having "an immunological activity equivalent to that of a polypeptide consisting of the amino acid sequence of SEQ ID NO: X" refers to a polypeptide having at least 70%, at least 80%, at least 90%, or at least 95% of the immunological activity of the polypeptide consisting of the amino acid sequence of SEQ ID NO: X. The immunological activity of a polypeptide can be confirmed by a method known in the art or in accordance with the method as described in Examples of the present application, for example by determination of inhibitory activity on malaria parasite growth of an antibody obtained from an animal immunized with the polypeptide. The immunological activity of a polypeptide can also be confirmed by administration of the polypeptide to a malaria infection model.

The polypeptide of the present invention may be provided in the form of a conjugate wherein the polypeptide is covalently linked to a conventionally known carrier via a linker, or as a chimera peptide comprising the polypeptide hybridized to a conventionally known carrier peptide. Such a conjugate and a hybrid are included in the scope of the present invention.

Examples of the carrier to which the polypeptide of the present invention may be conjugated or hybridized include virus-like particles, lipid particles such as liposome, keyhole limpet hemocyanin, or a protein such as bovine serum albumin, CRM197 or extracellular Pseudomonas aeruginosa toxin A.

The linker used for covalently linking a polypeptide of the present invention to a carrier may be a homo-difunctional linker or a hetero-difunctional linker. Examples of the homo-difunctional linker include N,N'-disuccinimidyl suberate or 1,4-bis(maleimido)butane. Examples of the hetero-difunctional linker include 3-sulfo-N-succinimidyl 4-(N-maleimidomethyl) cyclohexane-1-carboxylate sodium salt, or 1-ethyl-3-(3-dimethylaminopropyl)carbodiimide hydrochloride.

A hybrid of a polypeptide of the present invention and a carrier can be prepared on the basis of a corresponding amino acid sequence, or a nucleotide sequence encoding the amino acid sequence, as described for the polypeptide of the present invention.

3. Polynucleotide

In an aspect, the present invention provides a polynucleotide consisting of a nucleotide sequence encoding a polypeptide of the present invention (hereinafter, referred to as "polynucleotide of the present invention"). More specifically, the polynucleotide of the present invention may be a polynucleotide encoding a polypeptide consisting of the amino acid sequence of SEQ ID NO: 4 which corresponds to the amino acid sequence at positions 720 to 934 of SEQ ID NO: 2, or the amino acid sequence of SEQ ID NO: 8 which corresponds to the amino acid sequence at positions 648 to 830 of SEQ ID NO: 2, or a polypeptide consisting of an amino acid sequence substantially the same as SEQ ID NO: 4 or SEQ ID NO: 8. The polynucleotide of the present invention may be a single-stranded or double-stranded DNA or RNA.

The polynucleotide consisting of a nucleotide sequence encoding a polypeptide consisting of an amino acid sequence substantially the same as SEQ ID NO: 4 or SEQ ID NO: 8 includes:
(a) a polynucleotide consisting of a nucleotide sequence encoding an amino acid sequence that differs from the amino acid sequence of SEQ ID NO: 4 or 8 by substitution, deletion, addition, or insertion of 1 to 10 amino acid residues, preferably 1-5 amino acid residues, more preferably 1, 2 or 3 amino acid residues, and
(b) a polynucleotide consisting of a nucleotide sequence encoding an amino acid sequence that has at least 95%, preferably at least 97%, or more preferably at least 99% sequence identity with the amino acid sequence of SEQ ID NO: 4 or SEQ ID NO: 8.

Examples of the polynucleotide of the present invention include a polynucleotide consisting of the nucleotide sequence of SEQ ID NO: 3, and a polynucleotide consisting of the nucleotide sequence of SEQ ID NO: 7. Further examples of the polynucleotide of the present invention include a polynucleotide consisting of the nucleotide sequence of any of SEQ ID NO: 6, SEQ ID NO: 9 and SEQ ID NO: 10. The nucleotide sequence of SEQ ID NO: 3 and other specific examples of nucleotide sequences disclosed herein are DNA nucleotide sequences, but may also be understood as corresponding RNA nucleotide sequences having uracil (U) instead of thymine (T) in the DNA nucleotide sequences.

The polynucleotide of the present invention may be connected to a promoter and/or a regulatory element which enables expression of the polypeptide of the present invention encoded by the polynucleotide in a host cell. Such a polynucleotide comprising the polynucleotide of the present invention as a protein-coding region, and a promoter and/or a regulatory element connected thereto is included in the scope of the present invention.

When the polynucleotide of the present invention is double stranded, it can be introduced into an expression vector to form a recombinant expression vector which expresses a polypeptide of the present invention. Such an expression vector is included in the scope of the present invention.

For preparing the expression vector of the present invention, any appropriate type of vector can be used depending on the type of a host to which the vector is introduced or other specific factors. The vector may be a plasmid, a phage vector, or a viral vector. For transfection to *E. coli*, a plasmid vector such as pUC118, pUC119, pBR322 or pCR3, or a phage vector such as λZAPII or λgt11 may be useful. For transfection to yeast, pYES2 or pYEUra3 may be useful. For transfection to an insect cell, a bacmid formed by use of pFastBac1, or pAcSGHisNT-A may be useful. For transfection to an animal cell, a plasmid vector such as pKCR, pCDM8, pGL2, pcDNA3.1, pRc/RSV or pRc/CMV, or a viral vector such as a retroviral vector, an adenoviral vector, or an adeno-associated viral vector may be useful. For transfection to a plant cell, Tobacco mosaic viral vector or Agrobacterial vector may be useful.

The vector of the present invention may optionally comprise a promotor for gene expression, a gene coding a signal sequence, a marker gene for screening of cells, or a terminator. Also, the vector of the present invention may comprise a sequence encoding a tag for a protein, such as Gp 67, thioredoxin, a His tag or GST (glutathione S-transferase) so as to express a protein with a tag fused thereto for facilitation of isolation or purification of the protein. A vector expressing such a fused protein may be a vector expressing a GST-fused protein (for example pGEX4T), a vector comprising a sequence encoding a tag such as Myc or His (for example, pcDNA3.1/Myc-His), or a vector expressing a protein fused to thioredoxin or a His tag (for example, pET32a). Such a vector may comprise a promoter (for example, lac, tac, trc, trp, CMV, or SV40 early promoter) for expression of a protein in a host cell.

The expression vector prepared as described above may then be introduced into a host to prepare a transfectant cell or plant. The host for the transfection may be E. coli, yeast, an insect cell, a mammalian cell, a plant cell, or a plant. Examples of the E. coli host include an E. coli strain such as DH10Bac, HB101 which is a strain of an E. coli K-12 cell line, C600, JM109, DH5α, or AD494(DE3). Examples of the yeast host include Saccharomyces cerevisiae. Examples of the animal cell host include an L929 cell, a BALB/c3T3 cell, a C127 cell, a CHO cell, a COS cell, a Vero cell, a Hela cell, or a 293-EBNA cell. Examples of the insect cell host include sf9. Examples of the plant host include *Nicotiana benthamiana*.

The expression vector of the present invention may be introduced into a host by a conventional technique appropriately selected depending on the type of the host, for example selected from calcium phosphate method, DEAE-dextran method, electroporation, transfection utilizing a lipid (Cellfectin II, Lipofectamine, Lipofectin; Gibco-BRL), transfection utilizing Agrobacterium, microinjection, or particle gun. A desired transformant can be isolated from the cells or plants obtained after the transfection step, by culturing them in a medium containing a suitable selection marker.

A transformant prepared as described above may be cultured or grown to produce a polypeptide of the present invention. A polypeptide produced may be purified by a conventional purification technique in biochemical field, such as salting-out, ion-exchange chromatography, adsorption chromatography, affinity chromatography, or gel filtration chromatography. When a polypeptide of the present invention is expressed as a polypeptide fused to thioredoxin, a His tag, GST or other tag, the tag-fused polypeptide can be isolated or purified by utilizing the characteristics of the particular tag or tag-fused polypeptide.

The polynucleotide of the present invention may be administered to an animal, after incorporated into a vector suitable for gene therapy, for example. Such a vector for gene therapy comprising a polynucleotide of the present invention is included in the scope of the present invention.

The vector for the gene therapy may be a viral vector such as retrovirus, lentivirus, adenovirus, adeno associated virus, herpesvirus, Sendai virus, vaccinia virus, pox virus, polio virus, or Sindbis virus. Retrovirus, adenovirus, adeno associated virus, or vaccinia virus is preferred. A non-viral vector such as a plasmid vector may also be used.

A cell which expresses a polynucleotide of the present invention produces a polypeptide of the present invention in vivo. Therefore, the polynucleotide or expression vector of the present invention is useful as a malaria vaccine.

4. Production of Polypeptide

The polypeptide of the present invention can be produced by a method utilizing a genetic recombination technique wherein a polypeptide of the present invention may be produced by a host cell transfected with a polynucleotide encoding the polypeptide, or by cell-free synthesis, a chemical synthesis method, or any other appropriate method known in the art, as described in detail below.

A polypeptide of the present invention can be produced on the basis of genetic information of SEQ ID NO: 1, SEQ ID NO: 3, SEQ ID NO: 7 or SEQ ID NO: 10 by a method comprising the steps of cloning DNA, constructing an expression vector, introducing the vector into a host, culturing the transformant, and isolating a polypeptide produced by the transformant from the culture. For the method, any of the expression vectors and hosts listed above is useful. The method may be performed by using procedures known to a person skilled in the art or described in a literature (Molecular Cloning, T. Maniatis et al., CSH Laboratory (1983), DNA Cloning, D M. Glover, IRL PRESS (1985)). A transformant cell or plant which expresses a polypeptide of the present invention is included in the scope of the present invention.

In an embodiment, the polypeptide of the present invention may be produced by protein expression in a cultured insect cell, for example in accordance with the method described in Rohrmann G F. Baculovirus Molecular Biology [Internet]. 3rd edition. Bethesda (Md.): National Center for Biotechnology Information (US); 2013, or in Examples of the present application. In one example, such a method may comprise the steps of introducing a gene encoding a polypeptide of the present invention into a vector, introducing the vector into *E. coli* for recombination of the gene into a bacmid, isolating a colony of bacteria having the bacmid, purifying the bacmid and introducing it into an insect cell. A viral fluid yielded from the initial sensitization may be used in the next sensitization. The steps of yielding a viral fluid and sensitization with the viral fluid may be repeated until a viral fluid at an optimal concentration for sensitization for expression of a desired polypeptide is obtained. The polypeptide product may be purified by adsorption to a nickel resin via a histidine tag fused to the polypeptide.

The polypeptide of the present invention can be produced in a cell-free system by a conventionally known cell-free synthetic method, for example in a wheat germ extract as described in WO 05/030954. In the method described in WO 05/030954, transcription or translation reaction is carried out in vitro in a wheat germ extract comprising ribosome, by addition to the extract a transcription or translation template, a substrate gene, amino acids, energy sources, ions, a buffer and other agents. When RNA is used as a template in such a system, the system may be hereinafter referred to as "cell-free translation system". When DNA is used as a template in such a system, the system additionally comprises an enzyme required for transcription reaction, such as RNA polymerase, and the system may be hereinafter referred to as "cell-free transcription/translation system". For producing a polypeptide of the present invention, an RNA transcribed from a DNA comprising a polynucleotide of the present invention may be used as a translation template, or a DNA comprising a polynucleotide of the present invention may be used as a transcription template to form a translation template in an in vitro synthesis system. Besides a polynucleotide sequence of the present invention, a translation template may comprise RNA polymerase recognition sequence (SP6, T3 or T7 promoter), or a sequence promoting translation in vitro (for example, Ω sequence or E01 sequence). A wheat germ extract is commercially available, for example as WEPRO® (CellFree Sciences), or may be prepared in accordance with a method described, for example, in Johnston, F. B. et al., Nature, 179, 160-161 (1957). A wheat germ extract may be prepared by extraction of wheat germ isolated from the wheat in accordance with the method described, for example in Erickson, A. H. et al., (1996) Meth. In Enzymol., 96, 38-50. For preparing a wheat germ extract, a method described in WO 03/064671 may also be useful. In an embodiment of the present invention, a DNA consisting of the polynucleotide sequence of SEQ ID NO: 6 or SEQ ID NO: 9, or an RNA transcribed therefrom is used as a template, as described in Examples below.

The polypeptide of the present invention can be chemically synthesized by a method conventionally used in peptide chemistry, for example a method described in Peptide Synthesis, Interscience New York, 1966; The Proteins, Vol. 2, Academic Press Inc., New York, 1976; peptide synthesis, Maruzen Co., LTD., 1975; Basics and Experiment of Peptide Synthesis, Maruzen Co., LTD., 1985; or Development of Pharmaceutical Product subsequent vol. 14, Peptide Synthesis, Hirokawa Shoten, 1991. The polypeptide of the present invention may be produced, for example, by Fmoc or Boc method of solid phase synthesis, or liquid phase synthesis by sequential condensation of Boc-amino acid or Z-amino acid in a liquid phase (wherein Fmoc means 9-fluorenylmethoxycarbonyl, Boc means t-butoxycarbonyl, and Z means benzyloxycarbonyl). A polypeptide as synthesized may be purified by a method as conventionally used in peptide chemistry, for example by chromatography (for example, silica gel column chromatography, ion exchange column chromatography, gel filtration or reversed-phase chromatography) or recrystallization from a solvent, for example an alcohol, such as methanol, ethanol or 2-propanol; an ether, such as diethyl ether; an ester, such as ethyl acetate; an aromatic hydrocarbon, such as benzene or toluene; a ketone, such as acetone; a hydrocarbon, such as hexane; an aprotic solvent, such as dimethylformamide or acetonitrile; water; or a mixture thereof. For further useful purification methods, reference can be made, for example, to Jikken Kagaku Kouza (The Chemical Society of Japan ed., Maruzen) vol. 1.

5. Antibody

In an aspect, the present invention provides an antibody specific to a polypeptide of the present invention (hereinafter referred to as "antibody of the present invention"). The term "antibody" used herein include polyclonal antibody, monoclonal antibody, chimeric antibody, single chain antibody, and a part of such an antibody, such as Fab or other antibody fragment expressed in an Fab library.

The antibody of the present invention can be prepared in accordance with a method known in the art (Current protocols in Molecular Biology edit. Ausubel et al. (1987) Publish. John Wiley and Sons. Section 11.12-11.13; Antibodies: A Laboratory Manual, Second Edition, Edward A. Greenfield, Cold Spring Harber Laboratory Press, New York 2013).

Specifically, a polyclonal antibody of the present invention can be obtained from serum taken from a non-human animal such as a domestic rabbit immunized with a polypeptide of the present invention which may be prepared by genetic recombination, cell-free synthesis, or chemical synthesis. A monoclonal antibody of the present invention can be prepared in a hybridoma cell formed by cell fusion of a splenocyte and a myeloma cell harvested from a non-human animal such as a mouse immunized with a polypeptide of the present invention (Current protocols in Molecular Biology edit. Ausubel et al. (1987) Publish. John Wiley and Sons. Section 11.4-11.11; Antibodies: A Laboratory Manual, Second Edition, Edward A. Greenfield, Cold Spring Harber Laboratory Press, New York 2013).

Production of an antibody to a polypeptide of the present invention in a host immunized with the polypeptide can be promoted by co-administration of an adjuvant appropriately selected depending on the type of the host. Examples of such an adjuvant include Freund's adjuvant, a mineral gel such as aluminum hydroxide, a surfactant such as lysolecithin, Pluronic polyol, a polyanion, a peptide, an oil emulsion, keyhole limpet hemocyanin, or dinitrophenol, or a human cell-derived adjuvant such as BCG (Bacillus Calmette-Guerin) or *Corynebacterium parvum* adjuvant.

Thus, an antibody specific to a polypeptide of the present invention and effective to neutralize the effect of Ripr can be obtained easily from an animal immunized with the polypeptide by a conventional method. The antibody of the present invention is useful, for example, in prevention of a severe disorder caused by infection with a malaria parasite, and also as an agent for use in affinity chromatography or immunological diagnosis based, for example, on immunoblotting, radioimmunoassay (RIA), enzyme-linked immunosorbent assay (ELISA), or fluorescent or luminescent immunoassay.

6. Pharmaceutical Composition

The polypeptide, the polynucleotide or the expression vector of the present invention, or the antibody of the present invention specific to a polypeptide of the present invention is useful for prevention of infection with a malaria parasite, prevention of development of malaria disease after infection with a malaria parasite, or treatment of malaria disease. In an embodiment of the present invention, the polypeptide, the polynucleotide, the expression vector or the antibody of the present invention is formulated into a pharmaceutical composition. In an embodiment, the pharmaceutical composition of the present invention is used as a malaria vaccine.

The pharmaceutical composition of the present invention may optionally comprise a pharmaceutically acceptable carrier, or an appropriate adjuvant which is able to improve immunization efficacy of the composition. In an alternative embodiment of the present invention, a pharmaceutical composition comprising the polypeptide, the polynucleotide, the expression vector or the antibody of the present invention and a pharmaceutically acceptable carrier may be administered as a mixture with, or in combination with, a composition comprising an adjuvant. In this embodiment of the present invention, a pharmaceutical composition of the present invention and a composition comprising an adjuvant may be provided in a single kit.

An adjuvant for the present invention may be selected from conventionally known adjuvants as described, for example, in Nature Medicine, 19, 1597-1608, 2013. Examples of adjuvants include a virus- or bacterium-derived agent or a derivative thereof, a cytokine, a plant-derived agent or a derivative thereof, a marine organism-derived agent or a derivative thereof, a mineral gel such as aluminum hydroxide, a surfactant such as lysolecithin or Pluronic polyol, or a polyanion.

The term "bacterium-derived agent or a derivative thereof" includes (i) a killed bacterium, (ii) cell wall skeleton (CWS) obtained from a bacterium, and (iii) a component isolated from a microorganism or a derivative thereof.

Examples of the killed bacterium (i) include a killed hemolytic streptococcus bacterium in a powder form (for example PICIBANIL; Chugai pharmaceutical), a suspension cocktail form of a killed bacterium (for example, Broncasma Berna; Sanwa Kagaku Kenkyusho), and a killed *Mycobacterium tuberculosis*.

Examples of CWS (ii) include CWS obtained from *Mycobacterium* (for example, CWS from *Mycobacterium bovis* BCG), CWS obtained from *Nocardia* (for example, CWS from *Nocardia rubra*), or CWS obtained from *Corynebacterium*.

Examples of the component isolated from a microorganism or a derivative thereof (iii) include microbial polysaccharides, such as *Mycobacterium tuberculosis* polysaccharides (for example Ancer, Zeria Pharmaceutical), *Basidiomycota polysaccharides* (for example, Lentinan, Ajinomoto; Krestin, Sankyo, Coriolus versicolor polysaccharides), a muramyl dipeptide (MDP)-related compound, a lipopolysaccharide (LPS), a Lipid A-related compound (MPL), a glycolipid trehalose dimycolate (TDM), a DNA from a bacterium (for example, CpG oligonucleotide), a nucleic acid from a virus, or a derivative thereof (for example, poly I:C).

A component isolated from a microorganism or a derivative thereof is commercially available, or may be obtained by isolation from a microorganism by a method as described, for example, in Cancer Res., 33, 2187-2195 (1973), J. Natl. Cancer Inst., 48, 831-835 (1972, J. Bacteriol., 94, 1736-1745 (1967), Gann, 69, 619-626 (1978), J. Bacteriol., 92, 869-879 (1966), J. Natl. Cancer Inst., 52, 95-101 (1974).

Examples of the "cytokine" include IFN-α, IL-12, GM-CSF, IL-2, IFN-γ, IL-18, or IL-15. The cytokine may be a naturally occurring cytokine and a recombinant cytokine. Such a cytokine may be commercially available. A recombinant cytokine may be prepared on the basis of a nucleotide sequence registered in a database of, for example, GenBank, EMBL or DDBJ by a method comprising the steps of cloning an appropriate gene, introducing the gene into an expression vector, and introducing the vector into a host cell for gene expression.

Examples of the "plant-derived agent or a derivative thereof" include a derivative of saponin such as Quil A (Accurate Chemical & Scientific Corp), or QS-21 (Aquila Biopharmaceuticals inc.), or glycyrrhizin (SIGMA-ALDRICH).

Examples of the "marine organism-derived agent or a derivative thereof" include a glycolipid derived from a poriferan, such as α-galactosyl ceramide.

The pharmaceutical composition of the present invention may be formulated in a dosage form such as an oil emulsion, a liposome, a particle comprising active agent molecules attached to a bead having a diameter of several micrometers, a lipid-bound dosage form, a microsphere, or a microcapsule.

A pharmaceutical composition of the present invention in the form of an oil emulsion can be a water-in-oil (w/o) emulsion, an oil-in-water (o/w) emulsion, or a water-in-oil-in-water (w/o/w) emulsion. A w/o emulsion may comprise an active ingredient in the aqueous dispersion phase. A o/W emulsion may comprise an active ingredient in the aqueous dispersion media. A w/o/w emulsion may comprise an active ingredient in the internal aqueous dispersion phase. A pharmaceutical composition in an emulsion form of the present invention can be prepared in accordance with a method as described, for example, in in JP H08-000985 A or JP H09-122476 A.

A pharmaceutical composition of the present invention may be formulated in the form of a liposome. A liposome is a vesicle formed of a lipid bilayer membrane and is able to encapsulate an active agent or an aqueous phase comprising an active agent in the membrane. Examples of the liposome-forming lipid include phosphatidylcholine and sphingomyelin. An additive such as dicetyl phosphate, phosphatidic acid or phosphatidylserine may be added to modify liposome charge and stabilize liposomes. A pharmaceutical composition in a liposome form of the present invention may be prepared by an ultrasonic method, ethanol injection, ether injection, inverse-phase evaporation, or French Press extraction.

A pharmaceutical composition of the present invention may be formulated in the form of a microsphere. A microsphere is a microparticle of a polymer matrix and is able to incorporate an active agent dispersed throughout the polymer matrix. As a matrix-forming polymer, a biodegradable polymer such as albumin, gelatin, chitin, chitosan, starch, polylactic acid, or poly(alkyl cyanoacrylate) may be used. A pharmaceutical composition in a microsphere form of the present invention may be prepared by a method as described, for example, in Eur. J. Pharm. Biopharm. 50: 129-146, 2000, or Dev. Biol. Stand. 92: 63-78, 1998, Pharm. Biotechnol. 10:1-43, 1997.

A pharmaceutical composition of the present invention may be formulated in the form of a microcapsule. A microcapsule is a microparticle having a structure that a core comprising an active agent is coated with a coating material. The coating on the core can be a film of a polymer material such as carboxymethyl cellulose, cellulose acetate phthalate, ethyl cellulose, gelatin, gelatin/gum acacia, nitrocellulose, polyvinyl alcohol, or hydroxypropyl cellulose. A pharmaceutical composition in a microcapsule form of the present invention may be prepared by coacervation, or interfacial polymerization.

The pharmaceutical composition of the present invention is useful for prevention of infection with a malaria parasite, prevention of development of malaria disease after infection with a malaria parasite, or treatment of malaria disease. The "prevention of infection with a malaria parasite" means preventing a host from infection with the malaria parasite. The "prevention of development of malaria disease after infection with a malaria parasite" means preventing a malaria parasite-infected host from developing any symptom of malaria disease including, for example, fever, headache, nausea, disturbance in consciousness, or renal failure. The "treatment of malaria disease" means controlling or reducing a symptom caused by infection with a malaria parasite.

The pharmaceutical composition of the present invention can be administered to a subject in any dosage form and by any administration route appropriately chosen depending on a particular purpose of the administration or a condition of the subject. The pharmaceutical composition of the present invention may be administered, for example intravenously, intraarterially, subcutaneously, intramuscularly, intradermally, intranasally, or orally, in an appropriate dosage form selected, for example, from an injectable formulation, a transdermal formulation, an inhalable formulation, a nasal formulation, or an oral formulation. Intramuscular administration, which is a typical route of vaccine administration, may be useful for the pharmaceutical composition of the present invention.

For transfecting a cell with a polynucleotide or an expression vector of the present invention, a viral vector or any other means or technique may be used (Nikkei Science, April 1994, pp. 20-45; The pharmaceuticals monthly, 36(1), 23-48(1994); Experimental Medicine, extra edition, 12(15), (1994); or references cited therein).

As a viral vector into which a polynucleotide of the present invention is introduced, a DNA virus or an RNA virus, such as retrovirus, lentivirus, adenovirus, adeno-associated virus, herpesvirus, Sendai virus, vaccinia virus, pox virus, polio virus, or Sindbis virus can be used. Retrovirus, adenovirus, adeno-associated virus, or vaccinia virus is preferred. Alternatively, an expression plasmid may directly be administered as a DNA vaccine, or transfection of a cell with a polynucleotide or an expression vector of the present invention may be performed by a liposome method, a lipofectin method, a microinjection method, a calcium phosphate method, or an electroporation method. A DNA vaccine, or transfection by a liposome method is preferred.

A polynucleotide or an expression vector of the present invention can be administered as a vaccine by direct administration to a subject (in vivo method), or by a method comprising harvesting a certain kind of cells from a subject, transfecting the cells ex vivo with the polynucleotide or the expression vector, and returning the transfected cells into the subject (ex vivo method) (Nikkei Science, April 1994, pp. 20-45; The pharmaceuticals monthly, 36(1), 23-48(1994); Experimental Medicine, extra edition, 12(15), (1994); or references cited therein. An in vivo method is preferred.

For administration by an in vivo method, a polynucleotide or expression vector of the present invention may be formulated into a liquid preparation, or typically a preparation for injection. A pharmaceutically acceptable carrier may be added to such a preparation. Alternatively, a polynucleotide or expression vector of the present invention may be encapsulated in a liposome or a liposome capable of membrane fusion (Sendai virus (HVJ)-liposome). Such a liposome may be formulated into a suspension in a medium, or into a lyophilized preparation or a centrifuged and lyophilized preparation. A vaccine may also be prepared from a culture of cells infected with a virus into which an expression vector comprising a polynucleotide of the present invention is introduced.

An appropriate dose or dosing schedule of a pharmaceutical preparation can be determined depending on a specific purpose of the administration of the preparation, the age or body weight of a recipient of the preparation, or other factor. A typical dose of the polypeptide of the present invention may be from 0.0001 mg to 1000 mg, preferably from 0.001 mg to 100 mg, or more preferably from 0.01 mg to 10 mg.

An appropriate dosing schedule of the pharmaceutical composition of the present invention can be determined depending on a specific purpose of the administration of the preparation, the age or body weight of a recipient of the preparation, or other factor. The pharmaceutical composition of the present invention may be administered as a single dose, or as repeated doses (for example, 2 to 5 doses) at intervals of several days or weeks. The pharmaceutical composition of the present invention may be administered in a dosing schedule comprising an initial vaccination, and an additional vaccination given after a certain period of time (for example, a period of one to ten years) for maintaining and boosting the immunity. For each of the initial vaccination and the additional vaccination, the pharmaceutical composition may be administered as a single dose, or as repeated doses (for example, 2 to 5 doses).

A pharmaceutical composition of the present invention may optionally comprise, in addition to a polypeptide of the present invention, one or more other known malaria vaccine antigens. Alternatively, a pharmaceutical composition of the present invention comprising a polypeptide of the present invention may be administered in combination with one or more other known malaria vaccine antigens. A pharmaceutical composition of the present invention and a composition comprising other malaria vaccine antigen may be combined before administration, or administered as separate preparations. A pharmaceutical composition comprising a polypeptide of the present invention and a composition comprising other malaria vaccine antigen may be provided in a single kit. Examples of other malaria vaccine antigen include CSP (circumsporozoite protein), TRAP (thrombospondin-related anonymous protein), MSP1 (merozoite surface protein-1), AMA-1 (apical membrane antigen 1), SERA5 (serine repeat antigen 5), GAMA (GPI-anchored micronemal antigen), EBA175 (erythrocyte binding antigen 175), RH5 (reticulocyte-binding protein homologue 5), Pfs25 (*Plasmodium falciparum* surface protein 25), and Pfs230 (*Plasmodium falciparum* surface protein 230), and analogs thereof. Such an analog can be a peptide fragment (partial peptide) of the antigen protein, an altered form of the antigen protein or a fragment thereof that differs from the original amino acid sequence by substitution, deletion, addition or insertion of one or more (preferably one or several) amino acid residues, or a fusion polypeptide of one or more sequences of the antigen proteins and fragments thereof.

The pharmaceutical composition of the present invention may optionally comprise, in addition to a polypeptide of the present invention, one or more other known vaccine antigens for infections other than malaria infection. Alternatively, a pharmaceutical composition of the present invention comprising a polypeptide of the present invention may be administered in combination with one or more other known vaccine antigens for infection other than malaria infection. A pharmaceutical composition comprising a polypeptide of the present invention and a composition comprising other vaccine antigen for infection other than malaria infection may be combined before administration, or administered as separate preparations. A pharmaceutical composition comprising a polypeptide of the present invention and a composition comprising other vaccine antigen for infection other than malaria infection may be provided in a single kit. Examples of infection other than malaria infection include polio infection, diphtheria infection, pertussis infection, and tetanus infection. Vaccine antigens for these infections for use in the present invention may be any known vaccine antigen, such as *Bordetella pertussis* protective antigen, diphtheria toxoid, tetanus toxoid, or inactivated poliovirus.

In an aspect of the present invention, the present invention provides a method for preventing infection with a malaria parasite, preventing development of malaria disease after infection with a malaria parasite, or treating malaria disease, wherein the method comprising administering an effective amount of the pharmaceutical composition of the present invention to a human subject. The "effective amount" means an amount sufficient for achieving a desired effect of the prevention or treatment.

EXAMPLES

The present invention is illustrated in more detail in the following examples, but not limited to thereto.

Example 1

A vector comprising a wheat codon-optimized sequence encoding Ripr that was attached to a His-tag coding sequence at the C-terminus, named pEU-E01-MCS or a vector comprising a sequence of one of eleven fragments subcloned from the codon-optimized DNA for Ripr that was attached to a His-tag coding sequence at the C-terminus, named pEU-E01-GST-TEV-N2, was used as a template for transcription. All peptides were synthesized with templates that comprised a Met coding sequence at the N-terminus and a 6× His coding sequence at the C-terminus.

Wheat codon-optimized sequences encoding the amino acid sequences at positions 21 to 1086 of SEQ ID NO: 2, positions 720 to 934 of SEQ ID NO: 2 (SEQ ID NO: 4), and positions 648 to 830 of SEQ ID NO: 2 (SEQ ID NO: 8) are shown in SEQ ID NOs: 5, 6, and 9, respectively. The whole transcribed mRNA was used for protein synthesis with a wheat germ cell-free protein synthesis kit WEPRO® 7240H (cell free Science). The resulting solution containing the synthesized protein was affinity purified by using Ni Sepharose 6 Fast Flow (GE Healthcare). An antigen solution containing 0.1 mg or 0.14 mg polypeptide mixed with the same volume of Freund's complete adjuvant was subcutaneously administered to a rabbit for sensitization. After four weeks of the initial sensitization, an antigen solution containing 0.1 mg polypeptide mixed with the same volume of Freund's complete adjuvant was subcutaneously administered for additional sensitization. After six weeks of the initial sensitization, blood was collected from the rabbit and serum was obtained from the collected blood. IgGs were purified from the serum with HiTrap protein G Sepharose column (GE Healthcare). To the purified IgGs, normal human erythrocytes were added such that IgGs binding to the erythrocytes non-specifically were removed, and a polyclonal antibody was finally obtained. The polyclonal antibody, human erythrocytes, and erythrocytes infected with malaria parasites were mixed and cultured for 25 hours. After the culture, nuclei of the malaria parasites were stained with cyber green, and the number of malaria-infected erythrocytes was quantified by using FACS. The rate of growth inhibition of malaria parasites was calculated by determining a relative number of malaria-infected erythrocytes in the antibody-treated group when the number of malaria-infected erythrocytes in the untreated-group was considered 100, and further subtracting the relative number thus obtained from 100.

The following full length Ripr and 11 fragments (antigen peptides) were examined.

Ripr full (full length Ripr): a peptide consisting of the amino acid sequence at positions 21 to 1086 of SEQ ID NO: 2
Ripr 1-1: a peptide consisting of the amino acid sequence at positions 21 to 197 of SEQ ID NO: 2
Ripr 1-2: a peptide consisting of the amino acid sequence at positions 198 to 377 of SEQ ID NO: 2
Ripr 1-3: a peptide consisting of the amino acid sequence at positions 378 to 557 of SEQ ID NO: 2
Ripr 1-4: a peptide consisting of the amino acid sequence at positions 558 to 719 of SEQ ID NO: 2
Ripr 1-5: a peptide consisting of the amino acid sequence at positions 720 to 934 of SEQ ID NO: 2 (SEQ ID NO: 4)
Ripr 1-6: a peptide consisting of the amino acid sequence at positions 935 to 1086 of SEQ ID NO: 2
Ripr 2-1: a peptide consisting of the amino acid sequence at positions 108 to 287 of SEQ ID NO: 2
Ripr 2-2: a peptide consisting of the amino acid sequence at positions 288 to 467 of SEQ ID NO: 2
Ripr 2-3: a peptide consisting of the amino acid sequence at positions 468 to 647 of SEQ ID NO: 2
Ripr 2-4: a peptide consisting of the amino acid sequence at positions 648 to 830 of SEQ ID NO: 2 (SEQ ID NO: 8)
Ripr 2-5: a peptide consisting of the amino acid sequence at positions 831 to 1007 of SEQ ID NO: 2

The inhibitory activity on malaria parasite growth of the rabbit polyclonal antibody obtained by immunization of a rabbit with any of the full-length Ripr and 11 fragments (antigen peptides) is shown in FIG. 1. The result demonstrates that Ripr2-4 and Ripr1-5 peptides had inhibitory activity on malaria parasite growth, and also that Ripr1-5 peptide had a higher inhibitory activity on malaria parasite growth than the full length Ripr.

The amino acid sequences of Ripr1-5 and Ripr2-4 are shown below.

Ripr1-5
(SEQ ID NO: 4)
CDLSCPSNKVCVIENGKQTCKCSERFVLENGVCICANDYKMEDGINCIAK

NKCKRKEYENICTNPNEMCAYNEETDIVKCECKEHYYRSSRGECILNDYC

KDINCKENEECSIVNFKPECVCKENLKKNNKGECIYENSCLINEGNCPKD

SKCIYREYKPHECVCNKQGHVAVNGKCVLEDKCVHNKKCSENSICVNVMN

KEPICVCTYNYYKKD

Ripr2-4
(SEQ ID NO: 8)
STCYGNRFNYDCFCDNPYISKYGNKLCERPNDCESVLCSQNQVCQILPND

KLICQCEEGYKNVKGKCVPDNKCDESCPSNKVCVIENGKQTCKCSERFVL

ENGVCICANDYKMEDGINCIAKNKCKRKEYENICTNPNEMCAYNEETDIV

KCECKEHYYRSSRGECILNDYCKDINCKENEEC

Example 2

A baculovirus codon-optimized sequence encoding Ripr1-5 (SEQ ID NO: 10) that was attached to a gp67 secretion signal coding sequence at the N-terminus and a His-tag coding sequence at the C-terminus was subcloned into pFastBac1 vector. By using the expression vector thus obtained and DH10Bac competent cells, a recombinant bacmid was prepared. The recombinant bacmid was transfected into Sf9 insect cells with Cellfectin II reagents to produce a recombinant baculovirus. The recombinant baculovirus was amplified and Sf9 insect cells were infected with the recombinant baculovirus to express Ripr1-5. The culture supernatant was collected and Ripr1-5 was purified with Ni-NTA affinity column and Superdex 200 gel filtration column.

Figure 2:
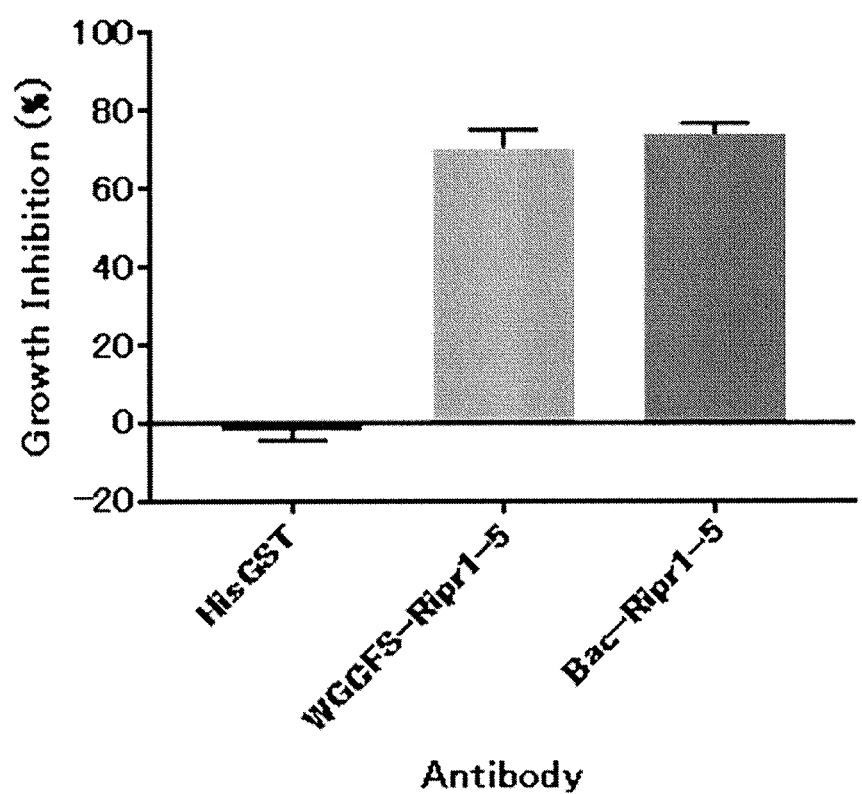
FIG. 2 shows the rate of growth inhibition of malaria parasites with a rabbit polyclonal IgG antibody obtained by immunization with Ripr1-5 produced in a wheat germ cell-free protein expression system (WGCFS-Ripr1-5) or in a baculovirus/insect cell expression system (Bac-Ripr1-5).

A rabbit polyclonal antibody was obtained by using Ripr1-5 produced by the baculovirus/insect cell expression system (Bac-Ripr1-5), in the same manner as in Example 1. The inhibitory activity on malaria parasite growth of the rabbit polyclonal antibody was compared with that of one rabbit polyclonal antibody of Example 1, which was obtained by immunization with Ripr1-5 produced by the wheat germ cell-free protein expression system (WGCFS- Ripr1-5). The result is shown in FIG. 2. This result demonstrates that the antibody induced with the Ripr1-5 peptide produced by the wheat germ cell-free protein expression system had comparable inhibitory activity on malaria parasite growth with the antibody induced with the Ripr1-5 peptide produced by the baculovirus/insect cell expression system.

INDUSTRIAL APPLICABILITY

The polypeptide, polynucleotide, expression vector, and antibody of the present invention are useful in the prevention of infection with a malaria parasite or development of malaria disease.

SEQUENCE FREE TEXT

SEQ ID NO: 3: Nucleotide sequence encoding the amino acid sequence at positions 720-934 of SEQ ID NO: 2 SEQ ID NO: 2

SEQ ID NO: 4: Amino acid sequence at positions 720-934 of SEQ ID NO: 2

SEQ ID NO: 5: Wheat codon-optimized sequence encoding the amino acid sequence at positions 21-1086 of SEQ ID NO: 2

SEQ ID NO: 6: Wheat codon-optimized sequence encoding the amino acid sequence at positions 720-934 of SEQ ID NO: 2

SEQ ID NO: 7: Nucleotide sequence encoding the amino acid sequence at positions 648-830 of SEQ ID NO: 2

SEQ ID NO: 8: Amino acid sequence at positions 648-830 of SEQ ID NO: 2

SEQ ID NO: 9: Wheat codon-optimized sequence encoding the amino acid sequence at positions 648-830 of SEQ ID NO: 2

SEQ ID NO: 10: Baculovirus codon-optimized sequence encoding the amino acid sequence at positions 720-934 of SEQ ID NO: 2

The invention claimed is:

1. A method of inhibiting growth of *Plasmodium falciparum* in a cell of a mammal, the method comprising administering to the mammal an immunogenic composition comprising a polypeptide consisting of the amino acid sequence of SEQ ID NO: 4.

2. The method according to claim 1, wherein the immunogenic composition further comprises, or is administered in combination with, at least one malaria vaccine antigen selected from circumsporozoite protein (CSP), thrombospondin-related anonymous protein (TRAP), merozoite surface protein-1 (MSP1), apical membrane antigen 1 (AMA-1), serine repeat antigen 5 (SERA5), GPI-anchored micronemal antigen (GAMA), erythrocyte binding antigen 175 (EBA175), reticulocyte-binding protein homologue 5 (RH5), *Plasmodium falciparum* surface protein 25 (Pfs25), and *Plasmodium falciparum* surface protein 230 (Pfs230).

3. The method according to claim 1, wherein the immunogenic composition further comprises, or is administered in combination with, a vaccine antigen against at least one infectious disease selected from polio, diphtheria, pertussis, and tetanus.

4. The method according to claim 1, wherein the method further comprises administering an adjuvant to the mammal.

5. A method of preventing development of malaria disease in a mammal having cells infected with *P. falciparum*, the method comprising administering to the mammal an immunogenic composition comprising a polypeptide consisting of the amino acid sequence of SEQ ID NO: 4.

6. The method according to claim 5, wherein the immunogenic composition further comprises, or is administered in combination with, at least one malaria vaccine antigen selected from CSP, TRAP, MSP1, AMA-1, SERA5, GAMA, EBA175, RH5, Pfs25, and Pfs230.

7. The method according to claim 5, wherein the immunogenic composition further comprises, or is administered in combination with, a vaccine antigen against at least one infectious disease selected from polio, diphtheria, pertussis, and tetanus.

8. The method according to claim 5, wherein the method further comprises administering an adjuvant to the mammal.

* * * * *